United States Patent [19]

DeSantis

[11] Patent Number: 4,567,044

[45] Date of Patent: Jan. 28, 1986

[54] LINIMENT COMPOSITION

[75] Inventor: Richard W. DeSantis, Monticello, N.Y.

[73] Assignee: Victory Lane Ltd., Monticello, N.Y.

[21] Appl. No.: 670,943

[22] Filed: Nov. 13, 1984

[51] Int. Cl.$^4$ ............................................. A61K 37/48
[52] U.S. Cl. ..................................... 424/94; 424/154; 514/472
[58] Field of Search ........................... 424/94; 514/472

[56] References Cited

U.S. PATENT DOCUMENTS 4,443,437  4/1984  Prokosch et al. ................... 424/195

OTHER PUBLICATIONS

Handbook of Non Prescription Drugs, 5th ed., pp. 289-295 (1977).

Primary Examiner—Leonard Schenkman
Attorney, Agent, or Firm—Bacon & Thomas

[57] ABSTRACT

The present invention relates to a liniment for application to animals, and in particular horses, which comprises as active ingredients, ammonium alum, dimethyl sulfoxide, goose oil, mineral oil, nitrofurazone and papain; the liniment may be topically applied to the animal such as for example on the horse's legs.

8 Claims, No Drawings

LINIMENT COMPOSITION

Liniments are well known for use to alleviate pain and soreness in animals caused by sprains and strains due to exercise and other activity. Liniments are often used prophylactically and/or after injury has occurred. Liniments include liquid or semi-liquid preparations and are commercially available in different strengths. The liniments may be applied directly as purchased or diluted to reduce the concentration of the active ingredients contained in the liniment.

The present invention relates to a novel liniment for application to animals, and in particular, horses. The invention also includes the treatment of soreness, swelling and strains and the prevention thereof in animals by the appropriate application of the liniment of the invention to the animal.

The liniment composition of the present invention contains as active ingredients ammonium alum, dimethyl sulfoxide, goose oil, mineral oil (petrolatum), nitrofurazone and papain. These ingredients are all known and commercially available. In addition to these ingredients other conventional ingredients and additives may be included in the composition. The composition as formulated can be applied directly to the appropriate portions of the animal's body. For example, the liniment, (optionally diluted) can be applied to the horse's legs by manually rubbing the liniment into the legs prior to and/or after exercise. Appropriate wrappings may also be used as is conventionally done with the application of liniments to horses.

More particularly, the liniment contains from 4–9 ounces of ammonium alum, 30–50 fluid ounces of dimethyl sulfoxide, 10–20 fluid ounces of goose oil, 5–15 fluid ounces of mineral oil and 20–30 fluid ounces of nitrofurazone (0.2% aqueous solution) and 4–10 grains of papain (papaya fruit). Most preferably, the composition contains, 4 ounces of ammonium alum, 40 fluid ounces of dimethyl sulfoxide, 10 fluid ounces of goose oil, 6 fluid ounces of mineral oil, 24 fluid ounces of nitrofurazone (0.2% aqueous solution) and 6 grains of papain (papaya fruit).

In addition, the liniment of the present invention may advantageously contain, from 4–10 ounces of aluminum acetate, 2–5 fluid ounces of coconut oil, 4–6 fluid ounces of lanolin oil, 3–5 fluid ounces of olive oil, 2–6 fluid ounces peanut oil, 4–8 fluid ounces of pine oil, 2–8 grains of salt (sodium chloride), 6–10 fluid ounces sassafras oil, 2–6 grains of sugar and 3–10 fluid ounces of wintergreen oil. Sufficient water may be added to the ingredients to obtain one gallon of liniment.

Accordingly, a liniment in accordance with the present invention will contain the following ingredients:

| | |
|---|---|
| Ammonium Alum (Solid) | 4–9 oz. |
| Aluminum Acetate (Solid) | 4–10 oz. |
| Coconut Oil | 2–5 oz. |
| Dimethyl Sulfoxide | 30–50 oz. |
| Goose Oil | 10–20 oz. |
| Lanolin Oil | 4–6 oz. |
| Mineral Oil | 5–15 oz. |
| Nitrofurazone .2% in a water soluble base | 20–30 oz. |
| Olive Oil | 3–5 oz. |
| Papain (Papaya Fruit (solid enzyme)) | 4–10 grains |
| Peanut Oil | 2–6 oz. |
| Pine Oil | 4–8 oz. |
| Salt (solid - sodium chloride) | 2–8 grains |
| Sassafras Oil | 6–10 oz. |
| Sugar (table) | 2–6 grains |
| Water | 8–12 oz. |
| Wintergreen Oil | 3–10 oz. |

Sufficient water may also be added to make one gallon of liniment.

A particularly preferred liniment composition contains the following ingredients per gallon:

| | |
|---|---|
| Ammonium Alum | 4 oz. |
| Aluminum Acetate-Topical solution | 4 oz. |
| Coconut Oil | 2 oz. |
| Dimethyl Sulfoxide | 40 oz. |
| Goose Oil | 10 oz. |
| Lanolin Oil | 4 oz. |
| Mineral Oil | 6 oz. |
| Nitrofurazone 0.2% in water soluble base | 24 oz. |
| Olive Oil | 3 oz. |
| Papain (Papaya Fruit) | 6 Grains |
| Peanut Oil | 4 oz. |
| Pine Oil | 5 oz. |
| Salt | 4 Grains |
| Sassafras Oil | 8 oz. |
| Sugar | 4 Grains |
| Water | 10 oz. |
| Wintergreen Oil | 4 oz. |

Sufficient water may also be added to make a gallon of liniment.

The liniment is preferably prepared by first mixing the ingredients most of which are already in liquid form. The aluminum acetate may first be added to a small amount of water before combining with the other ingredients. The mixing is conveniently performed in a blender. This results in a liniment which may be used directly or which may then be diluted by sufficient water to make a gallon of liniment. Obviously, the concentration of ingredients may vary within the range provided and the liniment may be diluted as necessary.

The liniment in accordance with the present invention may be used on horses for the treatment of bowed tendons and suspensory ligaments by massaging the leg liberally with liniment for 8–10 minutes. The leg is then wrapped with a clean stall bandage and then covered with plastic wrap, then stall wrapped. This is done immediately after the horse is exercised.

Sore or swollen knees and hocks may be treated by applying the liniment before the horse is exercised. Immediately after the horse is bathed, the joints are towelled dried and then the liniment is applied and the joints wrapped with a plastic wrap and covered with a knee or hock sweat-boot.

The hip and stifles of a horse may be treated by rubbing the liniment vigorously into the stifles and hips before and after exercise. If the horse has sore feet they may be treated by clipping the hair around the coronet band and then rubbing liniment into the coronet band. This procedure may be followed daily. As would be appreciated by anyone of ordinary skill in the art, the liniment of the present invention may be used in the same manner as commercially available liniments currently on the market to maintain the horse in sound condition. The liniment may also be used on humans.

I claim:

1. A liniment composition containing as active ingredients from 4–9 ounces of ammonium alum, 30–50 ounces of dimethyl sulfoxide, 10–20 ounces of goose oil, 5–15 ounces of mineral oil and 20–30 ounces of nitrofurazone (0.2% aqueous solution) and 4–10 grains of papain.

2. The liniment composition of claim 1 which contains about 4 ounces of ammonium alum, about 40 ounces of dimethyl sulfoxide, about 10 ounces of goose oil, about 6 ounces of mineral oil, about 24 ounces of nitrofurazone (0.2% aqueous solution) and about 6 grains of papain.

3. The liniment composition of claim 1 which also contains from 4–10 ounces of aluminum acetate, 2–5 ounces of coconut oil, 4–6 ounces of lanolin oil, 3–5 ounces of olive oil, 2–6 ounces peanut oil, 4–8 ounces of pine oil, 2–8 grains of salt, 6–10 ounces sassafras oil, 2–6 grains of sugar and 3–10 ounces of wintergreen oil.

4. The liniment composition of claim 3 which contains sufficient water to obtain one gallon of liniment.

5. The liniment composition of claim 3 which contains:

| Ammonium Alum | 4–9 oz. |
| --- | --- |
| Aluminum Acetate | 4–10 oz. |
| Coconut Oil | 2–5 oz. |
| Dimethyl Sulfoxide | 30–50 oz. |
| Goose Oil | 10–20 oz. |
| Lanolin Oil | 4–6 oz. |
| Mineral Oil | 5–15 oz. |
| Nitrofurazone .2% in a water soluble base | 20–30 oz. |
| Olive Oil | 3–5 oz. |
| Papain | 4–10 grains |
| Peanut Oil | 2–6 oz. |
| Pine Oil | 4–8 oz. |
| Salt | 2–8 grains |
| Sassafras Oil | 6–10 oz. |
| Sugar | 2–6 grains |
| Water | 8–12 oz. |
| Wintergreen Oil | 3–10 oz. |

6. The liniment composition of claim 5 which contains the following ingredients:

| Ammonium Alum | about 4 oz. |
| --- | --- |
| Aluminum Acetate | about 4 oz. |
| Coconut Oil | about 2 oz. |
| Dimethyl Sulfoxide | about 40 oz. |
| Goose Oil | about 10 oz. |
| Lanolin Oil | about 4 oz. |
| Mineral Oil | about 6 oz. |
| Nitrofurazone 0.2% in water soluble base | about 24 oz. |
| Olive Oil | about 3 oz. |
| Papain | about 6 Grains |
| Peanut Oil | about 4 oz. |
| Pine Oil | about 5 oz. |
| Salt | about 4 Grains |
| Sassafras Oil | about 8 oz. |
| Sugar | about 4 Grains |
| Wintergreen Oil | about 4 oz. |

7. A method for the treatment of bowed tendons and suspensory ligaments in an animal in need thereof which comprises massaging the leg of said animal liberally with the liniment composition of claim 3 for 8–10 minutes, wrapping the leg with a clean stall bandage and then covering with plastic wrap, then stall wrapping the leg.

8. A method for treating sore or swollen knees and hocks which comprises applying the liniment of claim 3 to the knees and hocks of a horse before the horse is exercised.

* * * * *